US010570202B2

(12) United States Patent
Martini et al.

(10) Patent No.: US 10,570,202 B2
(45) Date of Patent: Feb. 25, 2020

(54) COMBINATION OF A PD-1 ANTAGONIST AND A VEGFR INHIBITOR FOR TREATING CANCER

(71) Applicants: Pfizer Inc., New York, NY (US); Merck Sharp & Dohme Corp., Rahway, NJ (US)

(72) Inventors: Jean-Francois Andre Martini, Carlsbad, CA (US); Jamal Christo Tarazi, San Diego, CA (US); Rodolfo Fleury Perini, Philadelphia, PA (US); David J. Mauro, North Wales, PA (US)

(73) Assignees: Pfizer Inc., New York, NY (US); Merck Sharpe & Dohme Corp., Rahway, NJ (US)

( * ) Notice: Subject to any disclaimer, the term of this patent is extended or adjusted under 35 U.S.C. 154(b) by 0 days.

(21) Appl. No.: 15/115,730

(22) PCT Filed: Feb. 3, 2015

(86) PCT No.: PCT/US2015/014212
§ 371 (c)(1),
(2) Date: Aug. 1, 2016

(87) PCT Pub. No.: WO2015/119930
PCT Pub. Date: Aug. 13, 2015

(65) Prior Publication Data
US 2017/0166641 A1 Jun. 15, 2017

Related U.S. Application Data

(60) Provisional application No. 61/935,809, filed on Feb. 4, 2014.

(51) Int. Cl.
C07K 16/28 (2006.01)
A61K 39/395 (2006.01)
A61K 31/4439 (2006.01)
A61K 45/06 (2006.01)
C07K 16/30 (2006.01)

(52) U.S. Cl.
CPC ...... *C07K 16/2818* (2013.01); *A61K 31/4439* (2013.01); *A61K 39/39558* (2013.01); *A61K 45/06* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3053* (2013.01); *C07K 16/3061* (2013.01); *C07K 16/3069* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,534,524 B1 | 3/2003 | Kania | |
| 6,884,890 B2 | 4/2005 | Kania | |
| 7,141,581 B2 | 11/2006 | Bender | |
| 7,232,910 B2 | 6/2007 | Ewanicki | |
| 7,488,802 B2 | 2/2009 | Collins | |
| 7,521,051 B2 | 4/2009 | Collins | |
| 8,008,449 B2 | 8/2011 | Korman | |
| 8,168,757 B2 | 5/2012 | Finnefrock | |
| 8,354,509 B2 | 1/2013 | Carven | |
| 8,383,796 B2 | 2/2013 | Korman | |
| 8,791,140 B2 | 7/2014 | Campeta | |
| 8,900,587 B2 * | 12/2014 | Carven | C07K 16/2818 424/130.1 |
| 8,993,731 B2 | 3/2015 | Tyson | |
| 9,073,994 B2 | 7/2015 | Honjo et al. | |
| 9,220,776 B2 * | 12/2015 | Sharma | A61K 39/39591 |
| 9,457,019 B2 | 10/2016 | Flynn et al. | |
| 9,539,245 B2 | 1/2017 | Peters | |
| 9,683,048 B2 | 6/2017 | Freeman et al. | |
| 9,765,147 B2 | 9/2017 | Wong et al. | |
| 9,834,605 B2 * | 12/2017 | Carven | C07K 16/2818 |
| 9,993,551 B2 | 6/2018 | Lebwohl et al. | |
| 10,004,755 B2 | 6/2018 | Wang et al. | |
| 2004/0224988 A1 | 11/2004 | Freddo | |
| 2006/0091067 A1 | 5/2006 | Fan | |
| 2006/0094763 A1 | 5/2006 | Ye | |
| 2007/0203196 A1 | 8/2007 | Ewanicki | |
| 2008/0274192 A1 | 11/2008 | Friesen | |
| 2014/0099254 A1 * | 4/2014 | Chang | A61K 38/21 424/1.11 |
| 2014/0248347 A1 | 9/2014 | Morgado | |
| 2014/0288125 A1 | 9/2014 | Murray | |
| 2016/0159905 A1 | 6/2016 | Abdiche et al. | |
| 2017/0008971 A1 | 1/2017 | Dennis et al. | |
| 2017/0088626 A1 | 3/2017 | Jure-Kunkel et al. | |
| 2017/0158776 A1 | 6/2017 | Feltquate et al. | |
| 2017/0209574 A1 | 7/2017 | Cao et al. | |
| 2017/0296659 A1 | 10/2017 | Lebwohl et al. | |
| 2017/0298106 A1 | 10/2017 | Roschke et al. | |
| 2017/0320930 A1 | 11/2017 | Matzke-Ogi et al. | |
| 2018/0162941 A1 | 6/2018 | Thanavala | |
| 2018/0186882 A1 | 7/2018 | Freeman et al. | |

FOREIGN PATENT DOCUMENTS

| | | |
|---|---|---|
| WO | WO-2004072286 | 8/2001 |
| WO | WO-2004004771 | 1/2004 |

(Continued)

OTHER PUBLICATIONS

Equivalent Surface Area Dosage Factors (https://ncifrederick.cancer.gov/lasp/acuc/frederick/Media/Documents/ACUC42.pdf Aug. 2007) (Year: 2007).*

(Continued)

*Primary Examiner* — Peter J Reddig
(74) *Attorney, Agent, or Firm* — Arnold & Porter Kaye Scholer LLP

(57) ABSTRACT

The present disclosure describes combination therapies comprising an antagonist of Programmed Death 1 receptor (PD-1) and a VEGFR inhibitor, and the use of the combination therapies for the treatment of cancer, and in particular for treating cancers that express PD-L1.

26 Claims, 8 Drawing Sheets

Specification includes a Sequence Listing.

(56) References Cited

FOREIGN PATENT DOCUMENTS

| WO | WO-2004056875 | 7/2004 | |
|----|----|----|----|
| WO | WO-2006048745 | 5/2006 | |
| WO | 2008/100562 | 8/2008 | |
| WO | 2008/156712 | 12/2008 | |
| WO | WO-2010027827 | 3/2010 | |
| WO | WO-2010077634 | 7/2010 | |
| WO | WO-2011066342 | 6/2011 | |
| WO | WO-2012135408 A1 * | 10/2012 | ....... A61K 39/39591 |
| WO | WO-2013019906 | 2/2013 | |
| WO | 2013/164754 | 11/2013 | |
| WO | 2013/181452 | 12/2013 | |
| WO | 2014/163684 | 10/2014 | |
| WO | 2015/069266 | 5/2015 | |
| WO | 2016/059602 | 4/2016 | |

OTHER PUBLICATIONS

Ahmadzadeh et al., "Tumor antigen-specific CD8 T cells infiltrating the tumor express high levels of PD-1 and are functionally impaired," Blood, 114(8):1537-1544 (2009).

Clinical Trials: NCT02014636, "A Phase 1/11 Study to Assess the Safety and Efficacy of Pazopanib and MK 34 75 in Subjects With Advanced Renal Cell Carcinoma," ClinicalTrials.gov (Jan. 24, 2014), pp. 1-11. Retrieved from the Internet URL: https//clinicaltrials.gov/archive/NCT02014636/2014_01_24 [retrieved on Mar. 31, 2015] (11 pages).

Clinical Trials: NCT02133742, "A Phase 1 B, Open Label, Dose Finding Study to Evaluate Safety, Pharmacokinetics and Pharmacodynamics of Axitinib (AG-013736) in Combination With MK-34 75 in Patients With Advanced Renal Cell Cancer," ClinicalTrials.gov archive, (May 7, 2014), Retrieved from the Internet: URL:https:jjclinicaltrials.govjarchive/NCT 02133742/2014 05 07 [retrieved on-Mar. 30, 2015] (3 pages).

Clinical Trials: NCT02179918, "A Phase 1 Study of the 4-1B Agonsit PF-05082566 in Combination with the PD-1 Inhibitor MK-3475 in Patients with Advanced Solidy Tumors," Clinical Trials.gov (Jul. 1, 2014), pp. 1-6. Retrieved from the Internet URL: https://clinicaltrials.gov/archive/NCT02179918/2014_07_01 (6 pages).

Dong et al., "Tumor-associated B7-H1 promotes T-cell apoptosis: a potential mechanism of immune evasion," Nature Medicine, 8(8):793-800 (2002).

Duraiswamy et al., "Therapeutic PD-1 pathway blockade augments with other modalities of immunotherapy T-cell function to prevent immune decline in ovarian cancer," Cancer Research, 73(23):6900-6912 (2013).

Escudier et al., "Axitinib for the management of metastatic renal cell carcinoma," Drugs in R&D 11(2):113-126 (2011).

Gao et al., "Overexpression of PD-L1 significantly associates with tumor aggressiveness and postoperative recurrence in human hepatocellular carcinoma," Clinical Cancer Research, 15(3):971-979 (2009).

Ghebeh et al., "FOXP3+ Tregs and B7-H1+/PD-1+ T lymphocytes co-infiltrate the tumor tissues of high-risk breast cancer patients: Implication for immunotherapy," BMC Cancer, 8:57 (12 pages) (2008).

Ghebeh et al., "The B7-H1 (PD-L1) T lymphocyte-inhibitory molecule is expressed in breast cancer patients with infiltrating ductal carcinoma: correlation with important high-risk prognostic factors," Neoplasia, 8(3):190-198 (2006).

Hamanishi et al., "Programmed cell death 1 ligand 1 and tumor-infiltrating CD8+ T lymphocytes are prognostic factors of human ovarian cancer," Proceeding of the National Academy of Sciences, 104(9):3360-3365 (2007).

Hamid et al., "Safety and tumor responses with lambrolizumab (anti-PD-1) in melanoma," New England Journal of Medicine, 369(2):134-144 (2013).

Hino et al., "Tumor cell expression of programmed cell death-I ligand 1 is a prognostic factor for malignant melanoma," Cancer, 116(7):1757-1766 (2010).

Hu-Lowe et al., "Nonclinical antiangiogenesis and antitumor activities of axitinib (AG-013736), an oral, potent, and selective inhibitor of vascular endothelial growth factor receptor tyrosine kinases 1, 2, 3," Clinical Cancer Research, 14(22): 7272-7283 (2008).

Inman et al., "PD-L1 (B7-H1) expression by urothelial carcinoma of the bladder and BCG-induced granulomata: associations with localized stage progression," Cancer, 109(8):1499-1505 (2007).

McDermott et al., "PD-1 as a potential target in cancer therapy," Cancer Medicine, 2(5):662-673 (2013).

Nakanishi et al., "Overexpression of B7-H1 (PD-L1) significantly associates with tumor grade and postoperative prognosis in human urothelial cancers," Cancer Immunology, Immunotherapy, 56(8):1173-1182 (2007).

Nomi et al., "Clinical significance and therapeutic potential of the programmed death-1 ligand/programmed death-1 pathway in human pancreatic cancer," Clinical Cancer Research, 13(7):2151-2157 (2007).

Ohigashi et al., "Clinical significance of programmed death-1 ligand-1 and programmed death-1 ligand-2 expression in human esophageal cancer," Clinical Cancer Research, 11(8): 2947-2953 (2005).

PCT International Search Report, International Application No. PCT/US2015/014212, dated May 10, 2015 (12 pages).

Sharpe et al., "The function of programmed cell death 1 and its ligands in regulating autoimmunity and infection," Nature Immunology, 8(3):239-245 (2007).

Shimauchi et al., "Augmented expression of programmed death-1 in both neoplastic and non-neoplastic CD4+ T-cells in adult T-cell leukemia/lymphoma," International Journal of Cancer, 121(12):2585-2590 (2007).

Solowiej et al., "Characterizing the effects of the juxtamembrane domain on vascular endothelial growth factor receptor-2 enzymatic activity, autophosphorylation, and inhibition by axitinib," Biochemistry, 48(29):7019-31 (2009).

Thompson et al., "PD-1 is expressed by tumor-infiltrating immune cells and is associated with poor outcome for patients with renal cell carcinoma," Clinical Cancer Research, 13(6):1757 1761 (2007).

Thompson et al., "Significance of B7-H1 overexpression in kidney cancer," Clinical Genitourin Cancer, 5(3):206-211 (2006).

Wei et al., "Combinatorial PD-1 blockade and CD137 activation has therapeutic efficacy in murine cancer models and synergizes with cisplatin," PLOS One, 8(12):e84927 (11 pages) (2013).

Yang et al., "PD-L1: PD-1 interaction contributes to the functional suppression of T-cell responses to human uveal melanoma cells in vitro," Investigative Ophthalmology & Visusal Science, 49(6):2518-2525 (2008.

Yasuda et al., "Simultaneous blockade of programmed death 1 and vascular endothelial growth factor receptor 2 (VEGFR2) induces synergistic anti-tumour effect in vivo," Clinical and Experimental Immunology, 172(3):500-506 (2013).

Search Report dated Sep. 11, 2018 in ROC (Taiwan) Patent Application No. 104103603.

Yousaf et al., "Axitinib in advanced renal-cell carcinoma," The Lancet Oncology, 12(13):1245-1246 (2013).

Joshi, J., "ASCO GU 2018: Safety and Efficacy of Axitinib in Combination with Pembrolizumab in Patients with Advanced Renal Cell Cancer" available at www.urotoday.com (downloaded Oct. 19, 2018).

Procopio et al., "Combination Therapies for Patients with Metastatic Renal Cell Carcinoma," Lancet, 19:281-283 (2018).

Atkins et al., "Axitinib in Combination with Pembrolizumab in Patients with Advanced Renal Cell Carcinoma," presented at the European Society of Medical Oncology (ESM), Oct. 7-11, 2016, Copenhagen Denmark.

Rothermundt et al., "Successful treatment with an anti-PD-1 antibody for progressing brain metastases in renal cell cancer," Annals of Oncology, 25:544-552 (2016).

Topalian et al., "Safety, Activity, and Immune Correlates of Anti-PD-1 Antibody in Cancer," N. Engl. J. Med., 366(26):2443-2454 (2012).

Van Geel et al., "Concise Drug Review: Pazopanib and Axitinib," The Oncologist, 17:1081-1089 (2012).

(56) References Cited

OTHER PUBLICATIONS

Rini et al., "Pembrolizumab plus Axitinib versus Sunitinib for Advanced Renal-Cell Carcinoma," *The New England Journal of Medicine* 380:1116-1127 (2019).
FDA-Approved Patient Labeling for INLYTA, reference ID:3078397 (Jan. 2012).
Atkins et al., "Axitinib in Combination with Pembrolizumab in Patients with Advanced Renal Cell Cancer: a Non-Randomised, Open-Label, Dose-Finding, and Dose-Expansion Phase 1b Trial," *The Lancet Oncology*, 19(3):405-415 (2018).
Bai et al., "A Guide to Rational Dosing of Monoclonal Antibodies," *Clin. Pharmacokinet.*, 51(2):119-135 (2012).
Bailey et al., "Immune Checkpoint Inhibitors as Novel Targets for Renal Cell Carcinoma Therapeutics," *The Cancer Journal*, 19(4):348-352 (2013).
Choueiri et al., "Trial in Progress: Phase 1b Dose-Finding Study of Axitinib Plus Pembrolizumab for First-Line Treatment of Advanced Renal Cell Carcinoma (RCC)," *BJU International*, 114(Supp. 4):4-5 (Oct. 2014).
Czarnecka et al., "The Activity of Tyrosine Kinase Inhibitors on Clear Cell Renal Cell Carcinoma Tumor Initiating Cells in Hypoxic Microenvironment," *BJUI Supplements*, The 11th International Kidney Cancer Symposium Annual Meeting Proceedings, 110(Suppl. 2):1-20 (2012).
Domblides et al., "Emerging Antiangiogenics for Renal Cancer," *Expert Opinion on Emerging Drugs*, 18(4):495-511 (2013) (published online Dec. 2, 2013).
Dorff et al., "Novel Tyrosine Kinase Inhibitors for Renal Cell Carcinoma," *Expert Rev. Clin. Pharmacol.*, 7(1):67-73 (2014).
Escudier et al., "Optimal Management of Metastatic Renal Cell Carcinoma: Current Status," *Drugs*, 73:427-438 (2013).
European Search Report dated Mar. 21, 2019, issued in EP Application No. 18205542.
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (8 pages) (Study record version available online at clinicaltrials(dot)gov/ct2/history/NCT02133742 submitted Jun. 20, 2019).
Clinical Trial NTC02014636, "Safety and Efficacy Study of Pazopanib and MK 3475 in Advanced Renal Cell Carcinoma (RCC; Keynote-018)" (6 pages) (Study record version available online at https:clinicaltrials(dot)gov/ct2/history/NCT02014636 submitted Apr. 26, 2019).
Clinical Trial NCT02039674, "A Study of Pembrolizumab (MK-3475) in Combination with Chemotherapy or Immunotherapy in Participants with Non-Small Cell Lung Cancer (MK-3475-021/Keynote-021)" (5 pages) (Study record version available online at clinicaltrials(dot)gov/ct2/history/NCT02039674 submitted Jun. 12, 2019).
Clinical Trial NCT02039674, "A Study of Pembrolizumab (MK-3475) in Combination with Chemotherapy or Immunotherapy in Participants with Non-Small Cell Lung Cancer (MK-3475-021/Keynote-021)," (6 pages) (Study record version available online at clinicaltrials(dot)gov/ct2/history/NCT02039674 submitted Jan. 11, 2019).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (5 pages) (Study record version available online at clinicaltrials(dot)gov/ct2/history/NCT01472081 submitted Jun. 12, 2019).
Clinical Trial NCT01984242, "A Study of Atezolizumab (an Engineered Anti-Programmed Death-Ligand 1 [PD-L1] Antibody) as Monotherapy or in Combination with Bevacizumab (Avastin®) Compared to Sunitinib (Sutent®) in Participants with Untreated Advanced Renal Cell Carcinoma (IMmotion150)" (5 pages) (Study record version available online at clinicaltrials(dot)gov/ct2/history/NCT01984242 submitted Jun. 12, 2019).
Clinical Trial NCT02036502, "A study of Pembrolizumab (MK-3475) in Combination with Standard of Care Treatments in Participants with Multiple Myeloma (MK-3475-023/Keynote-023)" (5 pages) (Study record version available online at clinicaltrials(dot)gov/ct2/history/NCT02036502 submitted Apr. 24, 2018).
Clinical Trial NCT02331368, "Phase 2 Multi-Center Study of Anti-PD-1 during Lymphopenic State after HDT/ASCT for Multiple Myeloma" (4 pages) (Study record version available online at clinicaltrials(dot)gov/ct2/history/NCT02331368 submitted Jul. 2, 2018).
Clinical Trial NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (12 pages) (Study record version available online at clinicaltrials(dot)gov/ct2/history/NCT01472081 submitted Jun. 12, 2019).
Clinical Trial NCT02036502, "A study of Pembrolizumab (MK-3475) in Combination with Standard of Care Treatments in Participants with Multiple Myeloma (MK-3475-023/Keynote-023)" (11 pages) (Study record version available online at ClinicalTrials(dot)gov archive (submitted Apr. 24, 2018).
Clinical Trial NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (1 page) (Study record version available online at clinicaltrials(dot)gov/ct2/history/NCT02133742 submitted Jun. 20, 2019).
Kaufman et al., "The Society for Immunotherapy of Cancer Consensus Statement on Tumour Immunotherapy for the Treatment of Cutaneous Melanoma," *Nature*, 10:588-598 (2013).
Lipson et al., "Durable Cancer Regression Off-Treatment and Effective Reinduction Therapy with an Anti-PD-1 Antibody," *Clin. Cancer. Res.*, 19:462-468 (2013).
Pal et al., "Novel Therapies for Metastatic Renal Cell Carcinoma: Efforts to Expand beyond the VEGF/mTOR Signaling Paradigm," *Mol. Cancer Ther.*, 11(3):526-537 (2012).
Pardoll, "The Blockade of Immune Checkpoints in Cancer Immunotherapy," *Nature*, 12:252-264 (2012).
Patel et al., "Clinical Cancer Advances 2013: Annual Report on Progress Against Cancer from the American Society of Clinical Oncology," *J. Clin. Oncol.*, 32(2):129-160 (2014) (published online Dec. 10, 2013).
Patnaik et al., "Phase I Study of MK-3475 (Anti-PD-1 Monoclonal Antibody) in Patients with Advanced Solid Tumors," *J. Clin. Oncol.*, 30(Supp.15):2512 (2012).
Rini et al., "Five-Year Survival in Patients with Cytokine-Refractory Metastatic Renal Cell Carcinoma Treated with Axitinib," *Clin. Genitourin. Cancer*, 11(2):107-114 (2013).
Robert et al., "Drug of the Year: Programmed Death-1 Receptor/Programmed Death-1 Ligand-1 Receptor Monoclonal Antibodies," *European Journal of Cancer*, 49:2968-2971 (2013).
Robert et al., "LBA34-Pembrolizumab (Pembro:MK-3475) for Advanced Melanoma (MEL): Randomized Comparison of Two Dosing Schedules," *Annals of Oncology*, 25(Suppl.4):1-41 (Sep. 2014).
Sequence Listing from PCT/US2008/007463 filed Jun. 13, 2008.
Sliwkowski et al., "Antibody Therapeutics in Cancer," *Science*, 341:1192-1198 (2013).
Stehle et al., "Reduced Immunosuppressive Properties of Axitinib in Comparison with Other Tyrosine Kinase Inhibitors," *J. Biol. Chem.*, 288(23):16334-16347(2013).
Tang et al., "Programmed Death 1 Pathway Inhibition in Metastatic Renal Cell Cancer and Prostate Cancer," *Curr. Oncol. Rep.*, 15:98-104 (2013).
Tykodi, "Progress and Potential of Immune Checkpoint Blockage for Treating Advanced Renal Cell Carcinoma," *Immunotherapy*, 5(6):607-619 (2013).
*WHO Drug Information*, vol. 27, No. 2, pp. 161-162 (2013).

* cited by examiner hPD-1.08A light chain CDR1 (SEQ ID NO:1)

Arg Ala Ser Lys Ser Val Ser Thr Ser Gly Phe Ser Tyr Leu His hPD-1.08A light chain CDR2 (SEQ ID NO:2)

Leu Ala Ser Asn Leu Glu Ser hPD-1-08A light chain CDR3 (SEQ ID NO:3)

Gln His Ser Trp Glu Leu Pro Leu Thr hPD-1.08A heavy chain CDR1 (SEQ ID NO:4)

Ser Tyr Tyr Leu Tyr hPD-1.08A heavy chain CDR2 (SEQ ID NO:5)

Gly Val Asn Pro Ser Asn Gly Gly Thr Asn Phe Ser Glu Lys Phe Lys Ser hPD-1.08A heavy chain CDR3 (SEQ ID NO:6)

Arg Asp Ser Asn Tyr Asp Gly Gly Phe Asp Tyr

Fig. 1 hPD-1.09A light chain CDR1 (SEQ ID NO:7)
Arg Ala Ser Lys Gly Val Ser Thr Ser Gly Tyr Ser Tyr Leu His hPD-1.09A light chain CDR2 (SEQ ID NO:8)
Leu Ala Ser Tyr Leu Glu Ser hPD-1.09A light chain CDR3 (SEQ ID NO:9)
Gln His Ser Arg Asp Leu Pro Leu Thr hPD-1.09A heavy chain CDR1 (SEQ ID NO:10)
Asn Tyr Tyr Met Tyr hPD-1.09A heavy chain CDR2 (SEQ ID NO:11)
Gly Ile Asn Pro Ser Asn Gly Gly Thr Asn Phe Asn Glu Lys Phe Lys Asn hPD-1.09A heavy chain CDR3 (SEQ ID NO:12)
Arg Asp Tyr Arg Phe Asp Met Gly Phe Asp Tyr

Fig. 2

109A-H heavy chain variable region (SEQ ID NO:13)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys

Fig. 3

K09A-L-11 light chain variable region (SEQ ID NO:15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

Fig. 4

K09A-L-11 light chain full length (SEQ ID NO:18)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

K09A-L-16 light chain full length (SEQ ID NO:19)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Fig 5A

K09A-L-17 light chain full length (SEQ ID NO:20)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Fig. 5B

Heavy chain (SEQ ID NO:21)

| | | | | | |
|---|---|---|---|---|---|
| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Light chain (SEQ ID NO:22)

| | | | | | |
|---|---|---|---|---|---|
| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 219 |

Fig. 6

Nivolumab

Heavy chain (SEQ ID NO:23)

```
QVQLVESGGG VVQPGRSLRL DCKASGITFS NSGMHWVRQA PGKGLEWVAV  50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK            440
```

Light chain (SEQ ID NO:24)

```
EIVLTQSPAT LSLSPGERAT LSCRASQSVS SYLAWYQQKP GQAPRLLIYD  50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                       214
```

Fig. 7

COMBINATION OF A PD-1 ANTAGONIST AND A VEGFR INHIBITOR FOR TREATING CANCER

RELATED APPLICATIONS

This application is a United States National Stage under 35 U.S.C. § 371 of International Application No. PCT/US15/14212, filed Feb. 3, 2015 (pending), which claims the benefit of U.S. provisional application 61/935,809, filed on Feb. 4, 2014, which are incorporated by reference in their entireties.

SEQUENCE LISTING

The instant application contains a Sequence Listing which has been submitted electronically in ASCII format and is hereby incorporated by reference in its entirety. Said ASCII copy, created on Aug. 1, 2016, is named PCFC-956-301-SL.txt and is 32,580 bytes in size.

FIELD OF THE INVENTION

The present invention relates to combination therapies useful for the treatment of cancer. In particular, the invention relates to a combination therapy which comprises an antagonist of a Programmed Death 1 protein (PD-1) and an inhibitor of the vascular endothelial growth factor receptor (VEGFR) pathway.

BACKGROUND OF THE INVENTION

PD-1 is recognized as an important player in immune regulation and the maintenance of peripheral tolerance. PD-1 is moderately expressed on naive T, B and NKT cells and up-regulated by T/B cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

Protein tyrosine kinases have been identified as crucial targets in the therapeutic treatment of cancer. Growth factor ligands and their respective receptor tyrosine kinases are required for tumor angiogenesis and growth. Vascular endothelial growth factor (VEGF) is a critical component in the process leading to the branching, extension, and survival of endothelial cells forming new blood vessels during angiogenesis. Unwanted angiogenesis is a hallmark of several diseases, such as retinopathies, psoriasis, rheumatoid arthritis, age-related macular degeneration (AMD), and cancer (including solid tumors) Folkman, Nature Med., 1, 27-31 (1995).

Vascular endothelial growth factor receptor (VEGFR) inhibitors have been approved for the treatment of various types of cancer, including advanced and metastatic renal-cell carcinoma, gastrointestinal stromal tumors and hepatocellular carcinoma, and continue to be investigated in the clinical setting. It has been proposed that the efficacy of such inhibitors might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

SUMMARY OF THE INVENTION

In one embodiment, the invention provides a method for treating a cancer in an individual comprising administering to the individual a combination therapy which comprises a PD-1 antagonist and a VEGFR inhibitor.

In another embodiment, the invention provides a medicament comprising a PD-1 antagonist for use in combination with a VEGFR inhibitor for treating a cancer.

In yet another embodiment, the invention provides a medicament comprising a VEGFR inhibitor for use in combination with a PD-1 antagonist for treating a cancer.

Other embodiments provide use of a PD-1 antagonist in the manufacture of medicament for treating a cancer in an individual when administered in combination with a VEGFR inhibitor and use of a VEGFR inhibitor in the manufacture of a medicament for treating a cancer in an individual when administered in combination with a PD-1 antagonist.

In a still further embodiment, the invention provides use of a PD-1 antagonist and a VEGFR inhibitor in the manufacture of medicaments for treating a cancer in an individual. In some embodiments, the medicaments comprise a kit, and the kit also comprises a package insert comprising instructions for using the PD-1 antagonist in combination with a VEGFR inhibitor to treat a cancer in an individual.

In all of the above treatment method, medicaments and uses, the PD-1 antagonist inhibits the binding of PD-L1 to PD-1, and preferably also inhibits the binding of PD-L2 to PD-1. In some embodiments of the above treatment method, medicaments and uses, the PD-1 antagonist is a monoclonal antibody, or an antigen binding fragment thereof, which specifically binds to PD- or to PD-L1 and blocks the binding of PD-L1 to PD-1. In one embodiment, the PD-1 antagonist is an anti-PD-1 antibody which comprises a heavy chain and a light chain, and wherein the heavy and light chains comprise the amino acid sequences shown in FIG. 6 (SEQ ID NO:21 and SEQ ID NO:22).

In all of the above embodiments of the treatment method, medicaments and uses herein, the VEGFR inhibitor is N-methyl-2-[3-((E)-2-pyridin-2-yl-vinyl)-1H-indazol-6-yl-sulfanyl]-benzamide or a pharmaceutically acceptable salt thereof.

In some embodiments of the above treatment method, medicaments and uses of the invention, the individual is a human and the cancer is a solid tumor and in some embodiments, the solid tumor is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer. In some embodiments, the cancer is renal cell carcinoma (RCC). In some embodiments, the cancer is clear cell kidney cancer.

In other embodiments of the above treatment method, medicaments and uses of the invention, the individual is a human and the cancer is a Heme malignancy and in some embodiments, the Heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma. Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

Also, in some embodiments of any of the above treatment method, medicaments and uses, the cancer tests positive for the expression of one or both of PD-L1 and PD-L2. In still other embodiments, the cancer has elevated PD-L1 expression.

In one embodiment of the above treatment method, medicaments and uses, the individual is a human and the cancer is RCC that tests positive for human PD-L1.

In another embodiment of the above treatment method, medicaments and uses, the cancer is advanced RCC with clear cell subtype and is present in a human who has not been previously treated for RCC.

BRIEF DESCRIPTION OF THE DRAWINGS

FIG. 1 shows amino acid sequences of the light chain and heavy chain CDRs for an exemplary anti-PD-1 monoclonal antibody useful in the present invention (SEQ ID NOs: 1-6).

FIG. 2 shows amino acid sequences of the light chain and heavy chain CDRs for another exemplary anti-PD-1 monoclonal antibody useful in the present invention (SEQ ID NOs:7-12).

FIG. 3 shows amino acid sequences of the heavy chain variable region and full length heavy chain for an exemplary anti-PD-1 monoclonal antibody useful in the present invention (SEQ ID NO:13 and SEQ ID NO:14).

FIG. 4 shows amino acid sequences of alternative light chain variable regions for an exemplary anti-PD-1 monoclonal antibody useful in the present invention (SEQ ID NOs: 15-17).

FIGS. 5A-5B show amino acid sequences of alternative light chains for an exemplary anti-PD-1 monoclonal antibody useful in the present invention, with FIG. 5A showing the amino acid sequences for the K09A-L-11 and K09A-L-16 light chains (SEQ ID NOs: 18 and 19, respectively) and FIG. 5B showing the amino acid sequence for the K09A-L-17 light chain (SEQ ID NO:20).

FIG. 6 shows amino acid sequences of the heavy and light chains for MK-3475 (SEQ ID NOs. 21 and 22, respectively).

FIG. 7 shows amino acid sequences of the heavy and light chains for nivolumab (SEQ ID NOs. 23 and 24, respectively).

DETAILED DESCRIPTION

Abbreviations

Throughout the detailed description and examples of the invention the following abbreviations will be used:

BID One dose twice daily
CDR Complementarity determining region
CHO Chinese hamster ovary
DFS Disease free survival
DTR Dose limiting toxicity
FFPE formalin-fixed, paraffin-embedded
FR Framework region
IgG Immunoglobulin G
IHC Immunohistochemistry or immunohistochemical
MTD Maximum tolerated dose
NCBI National Center for Biotechnology Information
NCI National Cancer Institute
OR Overall response
OS Overall survival
PD Progressive disease
PFS Progression free survival
PR Partial response
Q2W One dose every two weeks
Q3W One dose every three weeks
QD One dose per day
RECIST Response Evaluation Criteria in Solid Tumors
SD Stable disease
VH Immunoglobulin heavy chain variable region
VK Immunoglobulin kappa light chain variable region I. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

"About" when used to modify a numerically defined parameter (e.g., the dose of a PD-1 antagonist or VEGFR inhibitor, or the length of treatment time with a combination therapy described herein) means that the parameter may vary by as much as 10% below or above the stated numerical value for that parameter. For example, a dose of about 5 mg/kg may vary between 4.5 mg/kg and 5.5 mg/kg.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3. CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum". "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Another particular example of cancer includes renal cell carcinoma. A further particular example of cancer includes clear cell kidney cancer. Cancers that may be treated in accordance with the present invention include those characterized by elevated expression of one or both of PD-L1 and PD-L2 in tested tissue samples.

"Biotherapeutic agent" means a biological molecule, such as an antibody or fusion protein, that blocks ligand/receptor signaling in any biological pathway that supports tumor maintenance and/or growth or suppresses the anti-tumor immune response.

"CDR" or "CDRs" as used herein means complementarity determining region(s) in a immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell proliferation or tumor growth. Chemotherapeutic agents useful in the treatment methods of the present invention include cytostatic and/or cytotoxic agents.

"Chothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

| Exemplary Conservative Amino Acid Substitutions | |
|---|---|
| Original residue | Conservative substitution |
| Ala (A) | Gly; Ser |
| Arg (R) | Lys; His |
| Asn (N) | Gln; His |
| Asp (D) | Glu; Asn |
| Cys (C) | Ser; Ala |

TABLE 1-continued

| Exemplary Conservative Amino Acid Substitutions | |
|---|---|
| Original residue | Conservative substitution |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide The terms "PD-L" and "mature PD-L" are used interchangeably herein, and shall be understood to mean the same molecule unless otherwise indicated or readily apparent from the context.

As used herein, a diagnostic anti-human PD-L mAb or an anti-hPD-L1 mAb refers to a monoclonal antibody that specifically binds to mature human PD-L1. A mature human PD-L1 molecule consists of amino acids 19-290 of the following sequence:

(SEQ ID NO: 25)
MRIFAVFIFMTYWHLLNAFTVTVPKDLYVVEYGSNMTIECKFPVEKQ

LDLAALIVYWEMEDKNIIQFVHGEEDLKVQHSSYRQRARLLKDQLSL

GNAALQITDVKLQDAGVYRCMISYGGADYKRITVKVNAPYNKINQRI

LVVDPVTSEHELTCQAEGYPKAEVIWTSSDHQVLSGKTTTTNSKREE

KLFNVTSTLRINTTTNEIFYCTFRRLDPEENHTAELVIPELPLAHPP

NERTHLVILGAILLCLGVALTFIFRLRKGRMMDVKKCGIQDTNSKKQ

SDTHLEET.

Specific examples of diagnostic anti-human PD-L1 mAbs useful as diagnostic mAbs for immunohistochemistry (IHC) detection of PD-L expression in formalin-fixed, paraffin-embedded (FFPE) tumor tissue sections are antibody 20C3 and antibody 22C3, which are described in the copending international patent application PCT/US13/075932, filed 18 Dec. 2013 and published as WO2014/100079 on 26 Jun.

2014. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P.R. China; Catalog number 10084-R015).

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in the treatment method, medicaments and uses of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6, nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by MedImmune.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MED14736, MSB0010718C and an antibody which comprises the heavy chain and light chain variable regions of SEQ ID NO:24 and SEQ ID NO:21, respectively, of WO2013/019906.

Other PD-1 antagonists useful in the any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

In some preferred embodiments of the treatment method, medicaments and uses of the present invention, the PD-1 antagonist is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other preferred embodiments of the treatment method, medicaments and uses of the present invention, the PD-1 antagonist is a monoclonal antibody, or antigen binding fragment thereof, which specifically binds to human PD-1 and comprises (a) a heavy chain variable region comprising SEQ ID NO: 13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In another preferred embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

In yet another preferred embodiment of the treatment method, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO: 18.

Table 2 below provides a list of the amino acid sequences of exemplary anti-PD-1 mAbs for use in the treatment method, medicaments and uses of the present invention, and the sequences are shown in FIGS. 1-5.

TABLE 2

EXEMPLARY ANTI-HUMAN PD-1 MONOCLONAL ANTIBODIES

A. Comprises light and heavy chain CDRs of hPD-1.08A in WO2008/156712

| | |
|---|---|
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |

B. Comprises light and heavy chain CDRs of hPD-1.09A in WO2008/156712

| | |
|---|---|
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

C. Comprises the mature h109A heavy chain variable region and one of the mature K09A light chain variable regions in WO2008/156712

| | |
|---|---|
| Heavy chain VR | SEQ ID NO: 13 |
| Light chain VR | SEQ ID NO: 15 or SEQ ID NO: 16 or SEQ ID NO: 17 |

D. Comprises the mature 409 heavy chain and one of the mature K09A light chains in WO2008/156712

| | |
|---|---|
| Heavy chain | SEQ ID NO: 14 |
| Light chain | SEQ ID NO: 18 or SEQ ID NO: 19 or SEQ ID NO: 20 |

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and realtime quantitative RT-PCR.

Several approaches have been described for quantifying PD-L1 protein expression in IHC assays of tumor tissue sections. See, e.g., Thompson. R. H., et al., *PNAS* 101 (49); 17174-17179 (2004); Thompson, R. H. et al., *Cancer Res.* 66:3381-3385 (2006); Gadiot, J., et al., *Cancer* 117:2192-

2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

"RECIST 1.1 Response Criteria" as used herein means the definitions set forth in Eisenhauer et al., E. A. et al., *Eur. J Cancer* 45:228-247 (2009) for target lesions or nontarget lesions, as appropriate based on the context in which response is being measured.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of a PD-1 antagonist and a VEGFR inhibitor to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:1S-10S (2009)). For example, with respect to tumor growth inhibition, according to NCI standards, a T/C ≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some preferred embodiments, response to a combination of the invention is any of PR, CR, PFS, DFS, OR or OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

The terms "treatment regimen", "dosing protocol" and "dosing regimen" are used interchangeably to refer to the dose and timing of administration of each therapeutic agent in a combination of the invention.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

"VEGFR inhibitor" means a small molecule inhibitor of vascular endothelial growth factor (VEGF) receptor or a monoclonal antibody against vascular endothelial growth factor (VEGF). In an embodiment, a "VEGFR inhibitor" means a small molecule inhibitor of vascular endothelial growth factor (VEGF) receptor. Specific VEGFR inhibitors useful as the VEGFR inhibitor in the treatment method, medicaments and uses of the present invention, include axitinib, sunitinib, sorafenib, tivozanib, and bevacizumab. In an embodiment, specific VEGFR inhibitors useful as the VEGFR inhibitor in the treatment method, medicaments and uses of the present invention, include axitinib, sunitinib, sorafenib, and tivozanib.

In an embodiment of the treatment method, medicaments and uses of the present invention, the VEGFR inhibitor is the compound, N-methyl-2-[3-((E)-2-pyridin-2-yl-vinyl)-1H-indazol-6-ylsulfanyl]-benzamide or 6-[2-(methylcarbamoyl)phenylsulfanyl]-3-E-[2-(pyridin-2-yl)ethenyl]indazole, of the following structure:

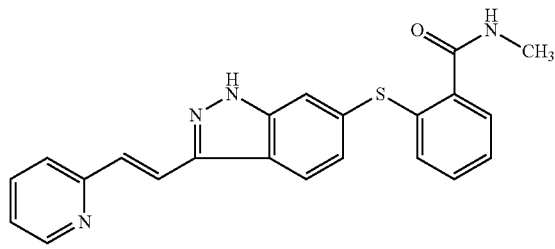 [SMILES: CNC(=O)c1ccccc1Sc1ccc2c(/C=C/c3ccccn3)n[nH]c2c1]

which is known as axitinib or AG-013736.

Axitinib is a potent and selective inhibitor of vascular endothelial growth factor (VEGF) receptors 1, 2 and 3. These receptors are implicated in pathologic angiogenesis, tumor growth, and metastatic progression of cancer. Axitinib has been shown to potently inhibit VEGF-mediated endothelial cell proliferation and survival (Hu-Lowe, D. D., et al., *Clin Cancer Res* 14: 7272-7283 (2008); Solowiej, S., et al., *Biochemistry* 48: 7019-31 (2009)). Clinical trials are currently on-going or have been conducted to study the use of axitinib for the treatment of various cancers, including liver cancer, melanoma, mesothelioma, non-small cell lung cancer, prostate cancer, renal cell carcinoma, soft tissue sarcomas and solid tumors. Inlyta® (axitinib) has been approved in the United States, Europe, Japan and other jurisdictions for the treatment of renal cell carcinoma.

Axitinib, as well as pharmaceutically acceptable salts thereof, is described in U.S. Pat. No. 6,534,524. Methods of making axitinib are described in U.S. Pat. Nos. 6,884,890 and 7,232,910, in U.S. Publication Nos. 2006-0091067 and 2007-0203196 and in International Publication No. WO 2006/048745. Dosage forms of axitinib are described in U.S. Publication No. 2004-0224988. Polymorphic forms and pharmaceutical compositions of axitinib are also described in U.S. Pat. No. 8,791,140 and U.S. Publication Nos. 2006-0094763, 2008-0274192, and 2014-0248347. Uses of axitinib, including use as a single agent or in combination treatment, are described in U.S. Pat. No. 7,141,581 and in U.S. Publication No. 2014-0288125. The patents and patent applications listed above are incorporated herein by reference.

Axitinib is understood to include reference to salts thereof, unless otherwise indicated. Axitinib is basic in nature and capable of forming a wide variety of salts with various inorganic and organic acids. The term "salt(s)", as employed herein, denotes acidic salts formed with inorganic and/or organic acids. Pharmaceutically acceptable salts of axitinib may be formed, for example, by reacting axitinib with an amount of acid, such as an equivalent amount, in a medium such as one in which the salt precipitates or in an aqueous medium followed by lyophilization.

Exemplary acid addition salts of axitinib include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

All such acid salts are intended to be pharmaceutically acceptable salts within the scope of axitinib, as used in the present invention and all acid salts are considered equivalent to the free forms of the corresponding compound for purposes of the invention.

Prodrugs of axitinib are also contemplated for use in the methods, medicaments and uses of the present invention. The term "prodrug", as employed herein, denotes a compound that is a drug precursor which, upon administration to a subject, undergoes chemical conversion by metabolic or chemical processes to yield axitinib or a salt thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

II. Methods, Uses and Medicaments

In one aspect of the invention, the invention provides a method for treating a cancer in an individual comprising administering to the individual a combination therapy which comprises a PD-1 antagonist and a VEGR inhibitor.

The combination therapy may also comprise one or more additional therapeutic agents. The additional therapeutic agent may be, e.g., a chemotherapeutic other than a VEGR inhibitor, a biotherapeutic agent (including but not limited to antibodies to VEGF, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastinc; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, the VEGFR inhibitor is administered before administration of the PD-1 antagonist, while in other embodiments, the VEGFR inhibitor is administered after administration of the PD-1 antagonist.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy of the invention can be administered orally or parenterally, including the intravenous, intramuscular, intraperitoneal, subcutaneous, rectal, topical, and transdermal routes of administration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation or by imaging techniques well known in the art, such as MRI, ultrasound, or CAT scan. In some preferred embodiments, a combination therapy of the invention is used to treat an advanced stage tumor having dimensions of at least about 200 mm 300 mm$^3$, 400 mm$^3$, 500 mm$^3$, 750 mm$^3$, or up to 1000 mm$^3$.

A combination therapy of the invention is preferably administered to a human patient who has a cancer that tests positive for PD-L1 expression. In some preferred embodiments, PD-L1 expression is detected using a diagnostic anti-human PD-L antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist and VEGFR inhibitor, but it is envisioned that the physician could order the first or subsequent diagnostic tests at any time after initiation of treatment, such as for example after completion of a treatment cycle.

Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*. Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist in the combination therapy, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein.

In one preferred embodiment of the invention, the PD-1 antagonist in the combination therapy is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist in the combination therapy is MK-3475, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, 10 mg Q3W and flat-dose equivalents of any of these doses, i.e., such as 200 mg Q3W. In some particularly preferred embodiments, MK-3475 is administered as a liquid medicament which comprises 25 mg/ml MK-3475, 7% (w/v) sucrose, 0.02% (w/v) polysorbate 80 in 10 mM histidine buffer pH 5.5, and the selected dose of the medicament is administered by IV infusion over a time period of about 30 minutes.

The optimal dose for MK-3475 in combination with axitinib may be identified by dose escalation of one or both of these agents. In one embodiment, axitinib is administered at 5 mg BID and MK-3475 is administered at a starting dose of 2 mg/kg Q2W, and if this dose combination is tolerated by the patient, the MK-3475 dose is increased up to a dose of 10 mg/kg Q2W, while if the starting dose combination is not tolerated by the patient, then the dose of MK-3475 is reduced to 1 mg/kg Q2W.

In another embodiment, axitinib is administered at 5 mg BID and MK-3475 is administered at a starting dose of 2 mg/kg Q3W, and if this starting dose combination is not tolerated by the patient, then the dose of MK-3475 is reduced to 1 mg/kg Q3W.

In another embodiment, axitinib is administered at 5 mg BID and MK-3475 is administered at a starting dose of 2 mg/kg Q3W, and if this dose combination is not tolerated by the patient, then the dose of axitinib is reduced to 3 mg BID.

In an embodiment, 5 mg of axitinib is administered with our without food BID, with each dose administered about 12 hours apart. On the day of MK-3475 administration, axitinib may be given prior to or after the MK-3475 administration.

In some embodiments, the patient is treated with a 7-day lead-in period of single-agent axitinib directly preceding the administration of the MK-3475 and axitinib combination.

In some embodiments, a treatment cycle begins with the first day of combination treatment and last for 2 weeks. In such embodiments, the combination therapy is preferably administered for at least 12 weeks (6 cycles of treatment), more preferably at least 24 weeks, and even more preferably at least 2 weeks after the patient achieves a CR.

In some preferred embodiments, the dose of axitinib is increased after 6 cycles if the patient tolerates axitinib with no drug-related grade >2 adverse events for 2 consecutive weeks. The axitinib dose may be increased by 2 mg BID each cycle up to a maximum dose of 10 mg BID.

In some embodiments, the patient is selected for treatment with the combination therapy of the invention is the patient has been diagnosed with advanced RCC with predominantly clear cell subtype, and the primary tumor has been resected. Preferably, the patient has not received prior systemic therapy for advanced RCC.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising MK-3475 that are suitable for use in the present invention. In some preferred embodiments, a medicament comprising MK-3475 is provided in a glass vial which contains about 50 mg of MK-3475.

The present invention also provides a medicament which comprises axitinib and a pharmaceutically acceptable excipient.

The anti-PD-1 and VEGFR inhibitor medicaments described herein may be provided as a kit which comprises a first container and a second container and a package insert. The first container contains at least one dose of a medicament comprising an anti-PD-1 antagonist, the second container contains at least one dose of a medicament comprising a VEGFR inhibitor, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some preferred embodiments of the kit, the anti-PD-1 antagonist is an anti-PD-1 antibody and the instructions state that the medicaments are intended for use in treating a patient having a cancer that tests positive for PD-L1 expression by an IHC assay.

These and other aspects of the invention, including the exemplary specific embodiments listed below, will be apparent from the teachings contained herein.

Exemplary Specific Embodiments of the Invention

1. A method for treating a cancer in an individual comprising administering to the individual a combination therapy which comprises a PD-1 antagonist and a VEGFR inhibitor.
2. The method of embodiment 1, wherein the PD-1 antagonist is a monoclonal antibody, or an antigen binding fragment thereof.
3. The method of embodiment 1 or 2, wherein the VEGFR inhibitor the compound N-methyl-2-[3-((E)-2-pyridin-2-yl-vinyl)-1H-indazol-6-ylsulfanyl]-benzamide or a pharmaceutically acceptable salt thereof.
4. A medicament comprising a PD-1 antagonist for use in combination with a VEGFR inhibitor for treating a cancer in an individual, wherein the PD-1 antagonist is a monoclonal antibody, or an antigen binding fragment thereof.
5. A medicament comprising a VEGFR inhibitor for use in combination with a PD-1 antagonist for treating a cancer in an individual.
6. The medicament of embodiment 4 or 5, which further comprises a pharmaceutically acceptable excipient.
7. Use of a PD-1 antagonist in the manufacture of medicament for treating a cancer in an individual when administered in combination with a VEGFR inhibitor.
6. Use of a VEGFR inhibitor compound in the manufacture of a medicament for treating a cancer in an individual when administered in combination with a PD-1 antagonist.
7. Use of a PD-1 antagonist and a VEGFR inhibitor in the manufacture of medicaments for treating a cancer in an individual.
8. A kit which comprises a first container, a second container and a package insert, wherein the first container comprises at least one dose of a medicament comprising an anti-PD-1 antagonist, the second container comprises at least one dose of a medicament comprising a VEGFR inhibitor, and the package insert comprises instructions for treating an individual for cancer using the medicaments.
9. The kit of embodiment 8, wherein the instructions state that the medicaments are intended for use in treating an individual having a cancer that tests positive for PD-L1 expression by an immunohistochemical (IHC) assay.
10. The method, medicament, use or kit of any of embodiments 1 to 9, wherein the individual is a human and the PD-1 antagonist is a monoclonal antibody, or an antigen binding fragment thereof, which specifically binds to human PD-L1 and blocks the binding of human PD-L to human PD-1.
11. The method, medicament, use or kit of embodiment 9, wherein the PD-1 antagonist is MPDL3280A. BMS-936559, MEDI4736, MSB0010718C or a monoclonal antibody which comprises the heavy chain and light chain variable regions of SEQ ID NO:24 and SEQ ID NO:21, respectively, of WO2013/019906.
12. The method, medicament, use or kit of any of embodiments 1 to 9, wherein the individual is a human, and the PD-1 antagonist is a monoclonal antibody, or an antigen binding fragment thereof, which specifically binds to human PD-1 and blocks the binding of human PD-L to human PD-1.
13. The method, medicament, use or kit of embodiment 12, wherein the PD-1 antagonist also blocks binding of human PD-L2 to human PD-1.
14. The method, medicament, use or kit of embodiment 13, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.
15. The method, medicament, use or kit of embodiment 13, wherein the monoclonal antibody, or antigen binding fragment thereof, comprises light chain CDRs of SEQ ID NOs: 7, 8 and 9 and heavy chain CDRs of SEQ ID NOs: 10, 11 and 12.
16. The method, medicament, use or kit of embodiment 13, wherein the PD-1 antagonist is an anti-PD-1 monoclonal antibody which comprises a heavy chain and a light chain, and wherein the heavy chain comprises SEQ ID NO:21 and the light chain comprises SEQ ID NO:22.
17. The method, medicament, use or kit of embodiment 13, wherein the PD-1 antagonist is an anti-PD-1 monoclonal antibody which comprises a heavy chain and a light chain, and wherein the heavy chain comprises SEQ ID NO:23 and the light chain comprises SEQ ID NO:24.

18. The method, medicament, use or kit of any of embodiments 10-17, wherein the cancer is a solid tumor.

19. The method, medicament, use or kit of any of embodiments 10-17, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer.

20. The method, medicament, use or kit of any of embodiments 10-17, wherein the cancer is advanced renal cell carcinoma.

21. The method, medicament, use or kit of any of embodiments 10-17, wherein the individual has not been previously treated for advanced renal cell carcinoma.

22. The method, medicament, use or kit of any of embodiments 10-17, wherein the cancer is clear cell kidney cancer.

23. The method, medicament, use or kit of any of embodiments 10-17, wherein the cancer is acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

24. The method, medicament, use or kit of any of embodiments 10-23, the cancer tests positive for human PD-L1.

25. The method, medicament, use or kit of embodiment 24, wherein the human PD-L1 expression is elevated.

26. The method, medicament, use or kit of embodiment 13, wherein the PD-1 antagonist is MK-3475 or nivolumab.

27. The method, medicament, use or kit of embodiment 26, wherein the MK-3475 is formulated as a liquid medicament which comprises 25 mg/ml MK-3475, 7% (w/v) sucrose, 0.02% (w/v) polysorbate 80 in 10 mM histidine buffer pH 5.5.

28. The method, medicament, use or kit of any of embodiments 1 to 27, wherein the VEGR inhibitor is sunitinib, sorafenib or tivozanib.

29. The method, medicament, use or kit of any of embodiments 1 to 27, wherein the VEGR inhibitor is N-methyl-2-[3-((E)-2-pyridin-2-yl-vinyl)-1H-indazol-6-ylsulfanyl]-benzamide or a pharmaceutically acceptable salt thereof.

30. The method, medicament, use or kit of any of embodiments 1 to 27, wherein the VEFR inhibitor is axitinib and is formulated as a 1 mg tablet or a 5 mg tablet.

31. A method for treating a human individual diagnosed with a cancer, comprising administering to the individual a combination therapy which comprises MK-3475 and axitinib, wherein (a) axitinib is administered at a dose of 5 mg BID and MK-3475 is administered at a dose selected from the group consisting of 1 mg/kg Q3W, 2 mg/kg Q3W and 200 mg Q3W or (b) axitinib is administered at a dose of 3 mg BID and MK-3475 is administered at a dose selected from the group consisting of 1 mg/kg Q3W, 2 mg/kg Q3W and 200 mg Q3W.

32. A medicament comprising MK-3475 for use in combination with axitinib for treating a cancer in a human individual by a method comprising administering to the individual (a) axitinib at a dose of 5 mg BID and MK-3475 at a dose selected from the group consisting of 1 mg/kg Q3W, 2 mg/kg Q3W and 200 mg Q3W or (b) axitinib at a dose of 3 mg BID and MK-3475 at a dose selected from the group consisting of 1 mg/kg Q3W, 2 mg/kg Q3W and 200 mg Q3W.

33. A medicament comprising axitinib for use in combination with MK-3475 for treating a cancer in a human individual by a method comprising administering to the individual (a) axitinib at a dose of 5 mg BID and MK-3475 at a dose selected from the group consisting of 1 mg/kg Q3W, 2 mg/kg Q3W and 200 mg Q3W or (b) axitinib at a dose of 3 mg BID and MK-3475 at a dose selected from the group consisting of 1 mg/kg Q3W, 2 mg/kg Q3W and 200 mg Q3W.

34. The method or medicament of any of embodiments 31 to 33, wherein axitinib is administered at a dose of 5 mg BID and MK-3475 is administered at 1 mg/kg Q3W.

35. The method or medicament of any of embodiments 31 to 33, wherein axitinib is administered at a dose of 5 mg BID and MK-3475 is administered at 2 mg/kg Q3W.

36. The method or medicament of any of embodiments 31 to 33, wherein axitinib is administered at a dose of 3 mg BID and MK-3475 is administered at 1 mg/kg Q3W.

37. The method or medicament of any of embodiments 31 to 33, wherein axitinib is administered at a dose of 3 mg BID and MK-3475 is administered at 2 mg/kg Q3W.

38. The method or medicament of any of embodiments 31 to 33, wherein axitinib is administered at a dose of 3 mg BID and MK-3475 is administered at 200 mg Q3W.

39. The method or medicament of any of embodiments 31 to 38, wherein the cancer is renal cell cancer.

40. The method or medicament of embodiment 39, wherein the individual has not been previously treated for renal cell cancer.

41. The method or medicament of any of embodiments 31 to 38, wherein the cancer is clear cell kidney cancer.

42. The method or medicament of any of embodiments 31 to 41, wherein a tissue section of the cancer removed from the individual prior to administration of the combination therapy tested positive for PD-L1 expression.

43. The method or medicament of embodiment 42, wherein at least 50% of the tumor cells in the tissue section tested positive for PD-L1 expression by an immunohistochemical (IHC) assay.

44. The method or medicament of embodiment 43, wherein the IHC assay employed the antibody 22C3 to detect PD-L1 expression.

45. The method or medicament of any of embodiments 31 to 44, wherein MK-3475 is administered by IV infusion.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*. Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley. Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997). *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature* Biotechnol. 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2<sup>nd</sup> ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Example 1: Treatment of Patients with Renal Cell Carcinoma with a Combination of Axitinib and MK-3475

This study will evaluate the efficacy of a combination of axitinib and MK-3475 in human patients with RCC. Patients will be treated with axitinib at 5 mg or 3 mg BID and with MK-3475 at 1 mg/kg or 2 mg/kg every three weeks by intravenous infusion for a period of 18 months.

TABLE 3 provides exemplary dosing information for the combination of axitinib and MK-3475.

| Dose Level | MK-3475 | Axitinib |
| --- | --- | --- |
| 1 (Starting Dose Level) | 2 mg/kg IV q3wk | 5 mg BID |
| 1a | 1 mg/kg IV q3wk | 5 mg BID |
| 1b | 2 mg/kg IV q3wk | 3 mg BID |

BID: twice daily;
q3wk: every 3 weeks.

It is expected that the combination of axitinib and MK-3475 will be more efficacious than either treatment alone according to at least one of the following outcome measures:

Duration of Response (DR) [Time Frame: 18 months]—Time in weeks from the first documentation of objective tumor response to objective tumor progression or death due to any cancer. Duration of tumor response will be calculated as (the date of the first documentation of objective tumor progression or death due to cancer minus the date of the first CR or PR that will be subsequently confirmed plus 1) divided by 7. DR will be calculated for the subgroup of participants with a confirmed objective tumor response.

Percentage of Participants With Objective Response [Time Frame: 18 months]-Percentage of participants with OR based assessment of confirmed complete remission (CR) or confirmed partial remission (PR) according to Response Evaluation Criteria in Solid Tumors (RECIST). Confirmed remission are those with repeat bone marrow showing less than 5 percent (%) myeloblasts with normal maturation of all cell lines and absolute values of the peripheral blood lasting at least 2 months. PR are those with all CR criteria except at least 50% decrease in the blasts over the pretreatment.

Progression-Free Survival (PFS) [Time Frame: 18 months]—Median time from the first dose of study treatment to the first documentation of objective tumor progression or to death due to any cause, whichever occurs first. PFS calculated as (Weeks)=(first event date minus first dose date plus 1) divided by 7.

Overall Survival (OS) [Time Frame: five years]—Overall survival will be the duration from enrollment to death. For participants who are alive, overall survival will be censored at the last contact.

Eastern Cooperative Oncology Group [ECOG] performance status [Time Frame: Up to 2.5 years]—ECOG-PS measured on-therapy (time between first dose and last dose date with a 30-day lag) assessed participant's performance status on 5 point scale: 0=Fully active/able to carry on all pre-disease activities without restriction;

1=restricted in physically strenuous activity, ambulatory/able to carry out light or sedentary work; 2=ambulatory (>50% of waking hrs), capable of all self care, unable to carry out any work activities; 3=capable of only limited self care, confined to bed/chair >50% of waking hrs; 4=completely disabled, cannot carry on any self care, totally confined to bed/chair; 5=dead.

Presence (rate) or absence of blood biomarkers [Time Frame: Up to 2.5 years]—To identify biomarkers (FGF, IL8, VEGF . . . ) of complete response and relapse/progression if occurs.

Patient eligibility for the study will be determined according to the following criteria:
Ages Eligible for Study: 18 Years and older.
Genders Eligible for Study: Both.
Accepts Healthy Volunteers: No.
Histologically or cytologically confirmed advanced RCC with predominantly clear-cell subtype with primary tumor resected;
at least one measurable lesion as defined by Response Evaluation Criteria In Solid Tumors (RECIST) version 1.1;
Eastern Cooperative Oncology Group performance status 0 or 1; and
controlled hypertension.

TABLE 4 provides a brief description of the sequences in the sequence listing.

| SEQ ID NO: | Description |
|---|---|
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | MK-3475 Heavy chain |
| 22 | MK-3475 Light chain |
| 23 | Nivolumab Heavy chain |
| 24 | Nivolumab light chain |
| 25 | Human PD-L1 |

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk propgnostic factors. *Neoplasia* (2006) 8: 190-198.
5. Hamanishi J et al. Programmed cell death 1 ligand 1 and tumor-infiltrating CD8+ T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother.* (2007) 56: 1173-1182.
13. Hino et al. Tumor cell expression of programmed cell death-1 is a prognostic factor for malignant melanoma. *Cancer* (2010): 00: 1-9.

14. Ghebeh H. Foxp3+ tregs and B7-H1+/PD-1+ T lymphocytes co-infiltrate the tumor tissues of high-risk breast cancer patients: implication for immunotherapy. *BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A method for treating a cancer in an individual comprising administering to the individual a combination therapy which comprises an antagonist of a Programmed Death 1 protein (PD-1) and a vascular endothelial growth factor receptor (VEGFR) inhibitor, wherein the PD-1 antagonist is an anti-PD-1 monoclonal antibody which comprises a heavy chain and a light chain, wherein the heavy and light chains comprise SEQ ID NO:21 and SEQ ID NO:22, respectively, and further wherein the VEGFR inhibitor is N-methyl-2-[3-((E)-2-pyridin-2-yl-vinyl)-1H-indazol-6-yl-sulfanyl]-benzamide or a pharmaceutically acceptable salt thereof.

2. The method of claim 1, wherein the individual is a human.

3. The method of claim 1, wherein the cancer is a solid tumor.

4. The method of claim 1, wherein the cancer is renal cell carcinoma.

5. The method of claim 1, wherein the PD-1 antagonist is Pembrolizumab and the VEGFR inhibitor is axitinib.

6. A kit which comprises a first container, a second container and a package insert, wherein the first container comprises at least one dose of a medicament comprising an antagonist of a Programmed Death 1 protein (PD-1), the second container comprises at least one dose of a medicament comprising a vascular endothelial growth factor receptor (VEGFR) inhibitor, and the package insert comprises instructions for treating an individual for cancer using the medicaments, wherein the PD-1 antagonist is an anti-PD-1 monoclonal antibody which comprises a heavy chain and a light chain, wherein the heavy and light chains comprise SEQ ID NO:21 and SEQ ID NO:22, respectively, and further wherein the VEGFR inhibitor is N-methyl-2-[3-((E)-2-pyridin-2-yl-vinyl)-1H-indazol-6-ylsulfanyl]-benzamide or a pharmaceutically acceptable salt thereof.

7. The kit of claim 6, wherein the instructions state that the medicaments are intended for use in treating an individual having a cancer that tests positive for Program Death-Ligand 1 (PD-L1) expression by an immunohistochemical (IHC) assay.

8. The kit of claim 6, wherein the individual is a human.

9. The kit of claim 6, wherein the PD-1 antagonist is Pembrolizumab formulated as a liquid medicament and the VEGFR inhibitor is axitinib formulated as a 1 mg tablet or a 5 mg tablet.

10. The method of claim 1, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), or small lymphocytic lymphoma (SLL).

11. The method of claim 10, wherein the cancer is advanced renal cell carcinoma.

12. A method for treating a human individual diagnosed with a cancer, comprising administering to the individual a combination therapy which comprises Pembrolizumab and axitinib, wherein (a) axitinib is administered at a dose of 5 mg twice daily (BID) and Pembrolizumab is administered at a dose selected from the group consisting of 1 mg/kg every three weeks (Q3W), 2 mg/kg Q3W and 200 mg Q3W or (b) axitinib is administered at a dose of 3 mg BID and Pembrolizumab is administered at a dose selected from the group consisting of 1 mg/kg Q3W, 2 mg/kg Q3W and 200 mg Q3W.

13. The kit of claim 6, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), or small lymphocytic lymphoma (SLL).

14. The method of claim 12, wherein said cancer is renal cell carcinoma.

15. The method of claim 12, wherein said Pembrolizumab is provided at a dose of 200 mg Q3W.

16. The method for treating a human individual diagnosed with a cancer of claim 12, comprising administering to the individual a combination therapy which comprises Pembrolizumab and axitinib, wherein axitinib is administered at a dose of 5 mg twice daily (BID) and Pembrolizumab is administered at a dose of 1 mg/kg every three weeks (Q3W).

17. The method for treating a human individual diagnosed with a cancer of claim 12, comprising administering to the individual a combination therapy which comprises Pembrolizumab and axitinib, wherein axitinib is administered at a dose of 5 mg twice daily (BID) and Pembrolizumab is administered at a dose of 2 mg/kg Q3W.

18. The method for treating a human individual diagnosed with a cancer of claim 12, comprising administering to the individual a combination therapy which comprises Pembrolizumab and axitinib, wherein axitinib is administered at a dose of 5 mg twice daily (BID) and Pembrolizumab is administered at a dose of 200 mg Q3W.

19. The method for treating a human individual diagnosed with a cancer of claim 12, comprising administering to the individual a combination therapy which comprises Pembrolizumab and axitinib, wherein axitinib is administered at a dose of 3 mg twice daily (BID) and Pembrolizumab is administered at a dose of 1 mg/kg every three weeks (Q3W).

20. The method for treating a human individual diagnosed with a cancer of claim 12, comprising administering to the individual a combination therapy which comprises Pembrolizumab and axitinib, wherein axitinib is administered at a dose of 3 mg twice daily (BID) and Pembrolizumab is administered at a dose of 2 mg/kg Q3W.

21. The method for treating a human individual diagnosed with a cancer of claim 12, comprising administering to the individual a combination therapy which comprises Pembrolizumab and axitinib, wherein axitinib is administered at a dose of 3 mg twice daily (BID) and Pembrolizumab is administered at a dose of 200 mg Q3W.

22. The kit of claim 9, wherein the PD-1 antagonist is Pembrolizumab formulated as a liquid medicament and the VEGFR inhibitor is axitinib formulated as a 1 mg tablet.

23. The kit of claim 9, wherein the PD-1 antagonist is Pembrolizumab formulated as a liquid medicament and the VEGFR inhibitor is axitinib formulated as a 5 mg tablet.

24. A method for treating renal cell carcinoma in an individual comprising administering to the individual a combination therapy which comprises an antagonist of a Programmed Death 1 protein (PD-1) and a vascular endothelial growth factor receptor (VEGFR) inhibitor, wherein the PD-1 antagonist is Pembrolizumab, and further wherein the VEGFR inhibitor is axitinib.

25. A method for treating advanced renal cell carcinoma in an individual comprising administering to the individual a combination therapy which comprises an antagonist of a Programmed Death 1 protein (PD-1) and a vascular endothelial growth factor receptor (VEGFR) inhibitor, wherein the PD-1 antagonist is Pembrolizumab, and further wherein the VEGFR inhibitor is axitinib.

26. The method of claim 1, wherein the PD-1 antagonist is Pembrolizumab.

\* \* \* \* \*

SEQUENCE LISTING

```
<160> NUMBER OF SEQ ID NOS: 25

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 4

Ser Tyr Tyr Leu Tyr
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Tyr Tyr Met Tyr
1               5

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80
```

Met Glu Leu Lys Ser Leu Gln Phe Asp Asp Thr Ala Val Tyr Tyr Cys
            85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
            115                 120

<210> SEQ ID NO 14
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
            85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 15
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 16
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30
```

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
        50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 18
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

```
Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 19
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

```
<210> SEQ ID NO 20
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80
```

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 22
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

```
<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125
```

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 24
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 25
<211> LENGTH: 290
<212> TYPE: PRT
<213> ORGANISM: Homo sapiens

<400> SEQUENCE: 25

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

```
Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
        275                 280                 285

Glu Thr
    290
```